(12) United States Patent
Terian et al.

(10) Patent No.: US 9,173,783 B1
(45) Date of Patent: Nov. 3, 2015

(54) ABSORBENT ARTICLE AND METHOD OF USE

(71) Applicant: Femme, LLC, New York, NY (US)

(72) Inventors: Juliana Terian, New York, NY (US); Lauren Giordano, New York, NY (US)

( * ) Notice: Subject to any disclaimer, the term of this patent is extended or adjusted under 35 U.S.C. 154(b) by 0 days.

(21) Appl. No.: 14/506,133

(22) Filed: Oct. 3, 2014

Related U.S. Application Data

(60) Provisional application No. 62/027,805, filed on Jul. 23, 2014, provisional application No. 62/044,768, filed on Sep. 2, 2014.

(51) Int. Cl.
*A61F 13/15* (2006.01)
*A61F 13/514* (2006.01)
*A61F 13/511* (2006.01)
*A61F 13/51* (2006.01)
*A61F 13/53* (2006.01)

(52) U.S. Cl.
CPC ..... *A61F 13/51496* (2013.01); *A61F 13/15203* (2013.01); *A61F 13/5116* (2013.01); *A61F 2013/15146* (2013.01); *A61F 2013/15243* (2013.01); *A61F 2013/5109* (2013.01); *A61F 2013/51178* (2013.01); *A61F 2013/530029* (2013.01); *A61F 2013/530481* (2013.01)

(58) Field of Classification Search
CPC .............. A61F 13/15747; A61F 2013/4708; A61F 13/47254
See application file for complete search history.

(56) References Cited

U.S. PATENT DOCUMENTS

| | | | | |
|---|---|---|---|---|
| 4,597,759 | A * | 7/1986 | Johnson | 604/385.16 |
| 4,820,294 | A * | 4/1989 | Morris | 604/383 |
| 2005/0148969 | A1 * | 7/2005 | Damay et al. | 604/378 |
| 2006/0276766 | A1 * | 12/2006 | Kentolall | 604/385.01 |
| 2008/0103474 | A1 * | 5/2008 | Luizzi | 604/387 |
| 2008/0300558 | A1 * | 12/2008 | Brusk et al. | 604/360 |
| 2009/0062762 | A1 * | 3/2009 | Himbergen et al. | 604/385.03 |
| 2009/0082744 | A1 * | 3/2009 | Hakansson et al. | 604/365 |
| 2009/0082749 | A1 * | 3/2009 | Scott et al. | 604/385.101 |
| 2014/0257224 | A1 * | 9/2014 | Hughes et al. | 604/385.01 |

* cited by examiner

*Primary Examiner* — Susan Su
(74) *Attorney, Agent, or Firm* — Richard Mark Blank, Esq.

(57) ABSTRACT

The present invention is an absorbent article, such as incontinence pads, absorbent personal pads for involuntary bladder elimination, feminine guards for incontinence, catamenial products, sanitary napkins, maxi pads, mini pads, liners, pantiliners, pads, nursing pads, menstruation tampons, sanitary tampons, tampons, feminine hygiene pads, menstruation pads, and sanitary pads. By allowing the user to utilize an absorbent article by itself, or multiple absorbent articles connected together, and by incorporating a unique design and shape, the present invention provides the user with a form-fitting and comfortable shape, maximum flexibility of use to conform to the user's body and garment type, an efficient means of catching of urine and/or other bodily liquids or discharges, the ability to hide the absorbent article underneath the user's undergarments regardless of the type, materials, or color of the undergarment worn, and the ability to hide pubic or other hair located underneath or protruding from the user's undergarments.

11 Claims, 12 Drawing Sheets

ABSORBENT ARTICLE AND METHOD OF USE

PRIORITY

This application claims the benefit of U.S. Provisional Utility Application No. 62/027,805 for the invention titled "ABSORBENT ARTICLE AND METHOD OF USE", which has a filing date of Jul. 23, 2014, and U.S. Provisional Utility Application No. 62/044,768 for the invention titled "ABSORBENT ARTICLE AND METHOD OF USE", which has a filing date of Sep. 2, 2014.

FIELD OF THE INVENTION

The present invention relates to absorbent articles such as incontinence pads, absorbent personal pads for involuntary bladder elimination, feminine guards for incontinence, catamenial products, sanitary napkins, maxi pads, mini pads, liners, pantiliners, pads, nursing pads, menstruation tampons, sanitary tampons, tampons, feminine hygiene pads, menstruation pads, sanitary pads, menstrual underwear, adult diapers, disposable adult diapers, disposable diapers for incontinence, incontinence diapers, personal hygiene products, feminine hygiene products, male hygiene products, incontinence garments, and incontinence products.

BACKGROUND OF THE INVENTION

An absorbent article for urine and/or other bodily liquid or discharge absorption, such as a pantiliner, sanitary napkin, or incontinence pad, when taken from its packaging, is commonly a "single size fits all" that is sold for use for a variety of different, individual body shapes and sizes, and garment styles, but does not take into account specific body and undergarment types or sizes, or other wants and desires of the user.

Some prior art discloses absorbent articles with perforated lines for the user to make their own adjustments for size, shape, style, type of garment, etc., by using utensils and tools, such as scissors, to actually perform their own operation on the product, which can be problematic for a variety of reasons including the waste of product due to errors made by the user when making their own adjustments during their operation on the product and user frustration at the required adjustments left to the user to administer.

There is prior art that discloses an absorbent article having removable portions that can reduce the dimensions of the article. The disclosed preferred embodiment in a prior art can be adjusted in size by tearing the absorbent article along one or more perforated lines and removing the portions that lie outside of said perforated lines. However, the resultant absorbent article of the prior art is commonly designed for garments having a full sized crotch portion and is not adaptable for thong garments. Additionally, the designs in prior art do not usually protect against leakage when there is a tear in or along the perforated lines. Other prior art discloses sanitary napkins capable of being elongated by unfolding pleats at the longitudinal ends and at least one adds a second absorbent element to a first element.

Further, a pad is easily visible when worn with any undergarment. If a pad is worn with an undergarment, lines of the pad become visible either directly by way of protrusions of the pad from the sides of the undergarment, or through the material, particularly if said pad is secured to an undergarment that is made of lace or similar material, or if the undergarments are tight around the user's body.

As described above, users that wear various types of undergarments often have the expense and bother of purchasing assorted sized protection products to meet their needs. In addition, pantiliners are often visible through, and inconvenient to be worn with underwear. Often, a user compromises and chooses only one size and color of incontinence protection even though such selection may be less than ideal for such user's needs.

Typical pads are designed for use with garments having a full sized crotch portion (e.g., briefs and bikinis.) However, such pads do not readily lend themselves for use with garments having an abbreviated crotch portion (e.g., thong garments.) As a result, many users purchase multiple types of sanitary and/or incontinent protection products so said users can be protected regardless of the type of underwear style they decide to wear.

Therefore, a need exists for a cost effective absorbent article that offers incontinence protection while also being adaptable to fit and work with various garments, and appear neutral and invisible behind the underwear regardless of whether such underwear be lace, thong, bikini, or any color and feel fresh and comfortable.

In at least one embodiment, the present invention has at least two multiple absorbent articles that can be attached together and/or separated by the user so any one of the absorbent articles can be used separately and alone, which provides the user with a maximum flexibility of use to conform to the user's body and garment type. In at least one embodiment of the present invention, the top sheet of the pad can form to the body in a curve, which aids in catching urine and/or other bodily liquids or discharges, and provides a form-fitting, comfortable shape for each user. In addition to the aiding in catching urine and/or other bodily liquids or discharges, and providing a form-fitting, comfortable shape for the user, the design of the present invention allows for its use with a variety of types or shapes of undergarment, and covers hair located around the pubic, crotch, or, in the case of female users, the vaginal areas of the body.

In at least one embodiment, the present invention hides neatly inside the undergarment of the wearer, regardless of whether the undergarment is lace, thong, cotton, bikini or other, by utilizing a "Back Sheet Cloaking Device" as defined herein in the "Definitions" section.

SUMMARY OF THE INVENTION

In one embodiment of the present invention, an Absorbent Article for wearing in certain areas, such as the crotch region of a wearer's undergarment, may comprise of at least one of each of the following: a liquid pervious top sheet on the side of the Absorbent Article that faces the body; a middle layer(s) comprising of at least one of the following: ADL, SAP and/or Fluff, and/or Air-Laid Paper; at least one liquid impervious Back Sheet Cloaking Device; the middle layer(s) is/are positioned between said liquid pervious top sheet and said at least one liquid impervious Back Sheet Cloaking Device; and the said at least one liquid impervious Back Sheet Cloaking Device is joined to said liquid pervious top sheet on the side of the Absorbent Article that faces the undergarment. Said Absorbent Article may be Pedestal Shaped, which can provide certain advantages such as less chafing of the skin, and a comfortable fit for the user. The top section of said Pedestal Shaped Absorbent Article may be significantly wider than the bottom end allowing for said Absorbent Article to cover hair in the pubic, pubic bone, and/or vaginal area. Said Absorbent Article may be Tapered Pedestal, which is designed to provide certain advantages such as less chafing of the skin, and a comfortable fit for the user. The top section of said Tapered Pedestal Shaped Absorbent Article may be significantly wider than the bottom end allowing for said Absorbent Article to cover hair in the pubic, pubic bone, and/or vaginal area. The top section of said Tapered Pedestal Shaped Absorbent Article may be additionally comprised of the Pubic and Vaginal Hair Hiding Device allowing for said Absorbent Article to cover hair in the pubic, pubic bone, and/or vaginal area. The top section of said Pedestal Shaped Absorbent Article may be additionally comprised of the Pubic and Vaginal Hair Hiding Device allowing for said Absorbent Article to cover hair in the pubic, pubic bone, and/or vaginal area. The Absorbent Article may have at least one of the following: at least one element thereof may be urine and/or other liquid absorbent; at least one element thereof may be odor absorbent and/or scented and/or a freshness device; at least one element thereof may provide UV and/or other sun screen or sun block protection; at least one element thereof may comprise in whole or in part at least one of the following: creams, lotions, moisturizers, medications, male and/or female hygiene products, bath powder; the top sheet may form to the user's body in a curve, which aids in catching urine and other liquids and/or discharges, and provides more comfort to the user; and/or the shape of the Absorbent Article may be a Non-Symmetrical Silhouette from top to bottom. The width of the top portion of the Absorbent Article may at least one of the following: at least 2" or greater; at least 3" or greater; at least 4" or greater; at least 5" or greater; between 2" and 3"; between 3" and 4"; or between 4" and 5". The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 140 and the upper end of 255, said Green may fall within the range bounded at the lower end of 100 and the upper end of 255, and said Blue may fall within the range bounded at the lower end of 80 and the upper end of 255. The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 150 and the upper end of 245, said Green may fall within the range bounded at the lower end of 110 and the upper end of 245, and said Blue may fall within the range bounded at the lower end of 90 and the upper end of 245. The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 210 and the upper end of 255, said Green may fall within the range bounded at the lower end of 140 and the upper end of 255, and said Blue may fall within the range bounded at the lower end of 140 and the upper end of 255. The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 220 and the upper end of 255, said Green may fall within the range bounded at the lower end of 150 and the upper end of 245, and said Blue may fall within the range bounded at the lower end of 150 and the upper end of 245. The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 110 and the upper end of 255, said Green may fall within the range bounded at the lower end of 60 and the upper end of 255, and said Blue may fall within the range bounded at the lower end of 50 and the upper end of 255. The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 120 and the upper end of 255, said Green may fall within the range bounded at the lower end of 70 and the upper end of 245, and said Blue may fall within the range bounded at the lower end of 60 and the upper end of 245.

In another embodiment of the present invention, an Adaptable Absorbent Article for wearing in certain areas, such as the crotch region of a wearer's undergarment, may comprise at least one of each of the following: at least two Absorbent Articles each comprising at least one of the following: a liquid pervious top sheet on the side of the Absorbent Article that faces the body; a middle layer(s) comprising of at least one of the following: ADL, SAP and/or Fluff, and/or Air-Laid Paper; at least one liquid impervious Back Sheet Cloaking Device; the middle layer(s) is/are positioned between said liquid pervious top sheet and said at least one liquid impervious Back Sheet Cloaking Device; and the said at least one liquid impervious Back Sheet Cloaking Device is joined to said liquid pervious top sheet on the side of the Absorbent Article that faces the undergarment. Said Adaptable Absorbent Article may be comprised of at least one Pedestal Shaped Absorbent Article and at least one Tapered Pedestal Shaped Absorbent Article. The top section of each of said Pedestal Shaped Absorbent Article and Tapered Pedestal Shaped Absorbent Article may be significantly wider than the bottom end so said Absorbent Articles cover the hair in the pubic and/or vaginal area and/or said Tapered Pedestal Shaped Absorbent Article may be significantly wider across the top section of the Absorbent Article so the Absorbent Article covers hair in the pubic, pubic bone, and/or vaginal area. The Adaptable Absorbent Article may have at least one of the following: at least one element thereof may be urine and/or other liquid absorbent; at least one element thereof may be odor absorbent and/or scented and/or a freshness device; at least one element thereof may provide UV and/or other sun screen or sun block protection; at least one element thereof may comprise in whole or in part at least one of the following: creams, lotions, moisturizers, medications, male and/or female hygiene products, bath powder; the top sheet may form to the user's body in a curve, which aids in catching urine and other liquids and/or discharges, and provides more comfort to the user; the shape of at least one of the Absorbent Article(s) may be a Non-Symmetrical Silhouette from top to bottom. The width of the top portion of at least one of the Absorbent Articles and/or the Adaptable Absorbent Article may be at least one of the following: at least 2" or greater; at least 3" or greater; at least 4"

or greater; at least 5" or greater; between 2" and 3"; between 3" and 4"; or between 4" and 5". The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 140 and the upper end of 255, said Green may fall within the range bounded at the lower end of 100 and the upper end of 255, and said Blue may fall within the range bounded at the lower end of 80 and the upper end of 255. The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 150 and the upper end of 245, said Green may fall within the range bounded at the lower end of 110 and the upper end of 245, and said Blue may fall within the range bounded at the lower end of 90 and the upper end of 245. The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 210 and the upper end of 255, said Green may fall within the range bounded at the lower end of 140 and the upper end of 255, and said Blue may fall within the range bounded at the lower end of 140 and the upper end of 255. The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 220 and the upper end of 255, said Green may fall within the range bounded at the lower end of 150 and the upper end of 245, and said Blue may fall within the range bounded at the lower end of 150 and the upper end of 245. The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 110 and the upper end of 255, said Green may fall within the range bounded at the lower end of 60 and the upper end of 255, and said Blue may fall within the range bounded at the lower end of 50 and the upper end of 255. The Back Sheet Cloaking Device may have a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red may fall within the range bounded at the lower end of 120 and the upper end of 255, said Green may fall within the range bounded at the lower end of 70 and the upper end of 245, and said Blue may fall within the range bounded at the lower end of 60 and the upper end of 245.

The foregoing description and specification of at least one current preferred embodiment of the invention has been presented for the purposes of illustration and description. While multiple embodiments are disclosed, other embodiments of the present invention will become apparent to those skilled in the art from this application, which shows and describes illustrative embodiments of the invention. As will be realized, the invention is capable of modifications in various obvious aspects, all without departing from the spirit and scope of the present invention. Accordingly, the detailed description is to be regarded as illustrative in nature and not restrictive. Also, although not explicitly recited, one or more embodiments of the invention may be practiced in combination or conjunction with one another. Furthermore, the reference or non-reference to a particular embodiment of the invention shall not be interpreted to limit the scope the invention. It is intended that the scope of the invention neither be limited by any section herein nor by the specific claims and the equivalents drafted herein.

DETAILED DESCRIPTION OF THE DRAWINGS

Figure 1:
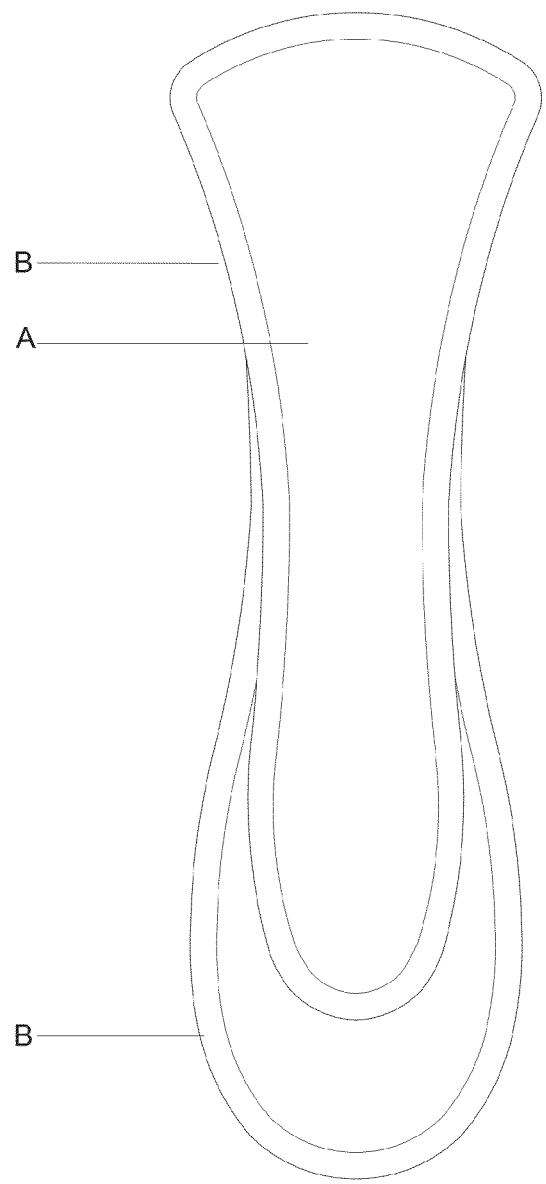
FIG. 1 shows a frontal view of an Adaptable Absorbent Article with two Absorbent Articles.

FIG. 1 shows a frontal view of the Adaptable Absorbent Article with two Absorbent Articles that can be attached together and/or separated by the user so any one of the Absorbent Articles can be used separately and alone, which provides the user with maximum flexibility of use to conform to the user's body and garment type. One of the Absorbent Articles (letter "A") of the Adaptable Absorbent Article in FIG. 1 is Tapered Pedestal Shaped, which is an oval shape in which the exterior silhouette or three-dimensional outline of an item has a top end and a bottom end with the top end being curved outward and wide, continuing and becoming more narrow, and continuing and becoming slightly wider at the bottom end. The top end of the Tapered Pedestal Shaped is significantly wider than the bottom end. The other Absorbent Article (letter "B") of the Adaptable Absorbent Article in FIG. 1 is Pedestal Shaped, which is an oval shape in which the exterior silhouette or three-dimensional outline of an item has a top end and a bottom end with the top end being curved outward and wide, continuing and becoming more narrow, and then continuing and becoming wider at the bottom end.

Figure 2:
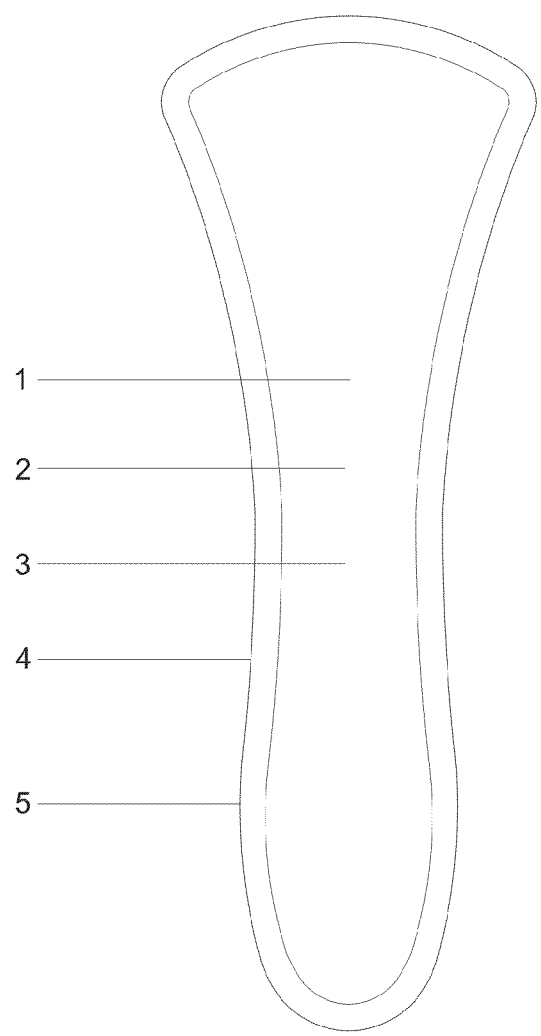
FIG. 2 shows a frontal view of an Absorbent Article that is Tapered Pedestal Shaped.

FIG. 2 shows a frontal view of an Absorbent Article that is Tapered Pedestal Shaped, which is an oval shape in which the exterior silhouette or three-dimensional outline of an item has a top end and a bottom end with the top end being curved outward and wide, continuing and becoming more narrow, and continuing and becoming slightly wider at the bottom end. The top end of the Tapered Pedestal Shape is significantly wider than the bottom end. FIG. 2 discloses a top sheet 1, which faces the body of the user, an ADL 2, and SAP/Fluff 3. The top sheet 1, ADL 2, and SAP/Fluff 3 are located on top of Air-Laid Paper 4, and a bottom sheet 5, which touches the garment and includes the Back Sheet Cloaking Device (not shown).

Figure 3:
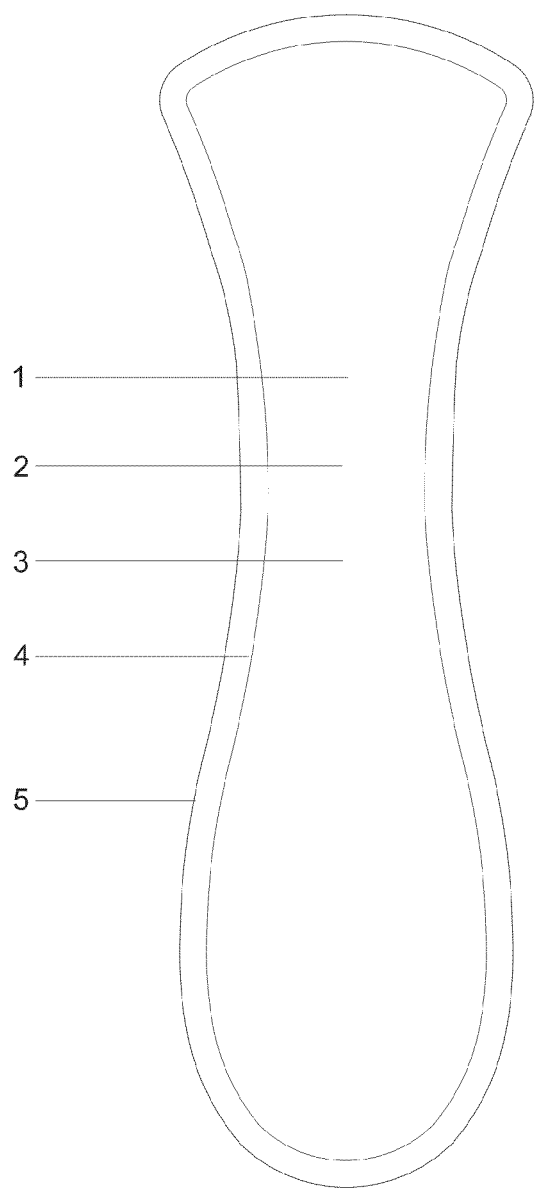
FIG. 3 shows a frontal view of an Absorbent Article that is Pedestal Shaped.

FIG. 3 shows a frontal view of an Absorbent Article that is Pedestal Shaped, with an exterior solid line that forms the entire exterior silhouette with a top end that curves outward, which forms the widest section of the exterior silhouette, an oval-shaped bottom end that curves outward, and sides that first taper and then enlarge between the top end and the bottom end, and an interior solid line close to the exterior solid line that follows the same or a substantially similar pattern as that of the exterior solid FIG. 3 discloses a top sheet 1, which faces the body of the user, an ADL 2, and SAP/Fluff 3. The top sheet 1, ADL 2, and SAP/Fluff 3 are located on top of Air-Laid Paper 4, and a bottom sheet 5, which touches the garment and includes the Back Sheet Cloaking Device (not shown).

Figure 4:
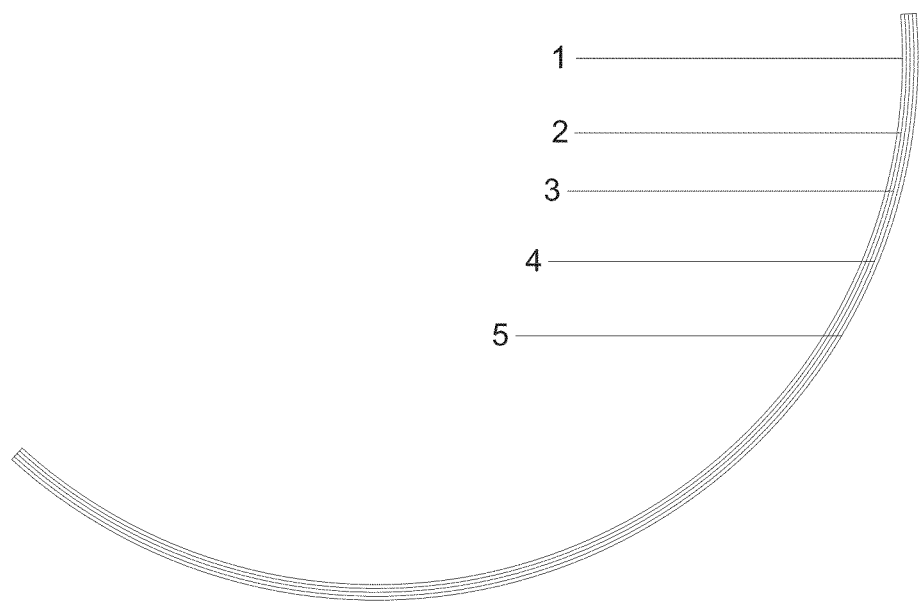
FIG. 4 shows a side view of an Absorbent Article that is Tapered Pedestal Shaped.

FIG. 4 shows a side view of an Absorbent Article that is Tapered Pedestal Shaped, which is an oval shape in which the exterior silhouette or three-dimensional outline of an item has a top end and a bottom end with the top end being curved outward and widest, continuing and becoming more narrow, and continuing and becoming slightly wider at the bottom end. The top end of the Tapered Pedestal Shape is significantly wider than the bottom end. FIG. 4 discloses a top sheet 1, which faces the body of the user, an ADL 2, and SAP/Fluff 3. The top sheet 1, ADL 2, and SAP/Fluff 3 are located on top of Air-Laid Paper 4, and a bottom sheet 5, which touches the garment and includes the Back Sheet Cloaking Device (not shown).

Figure 5:
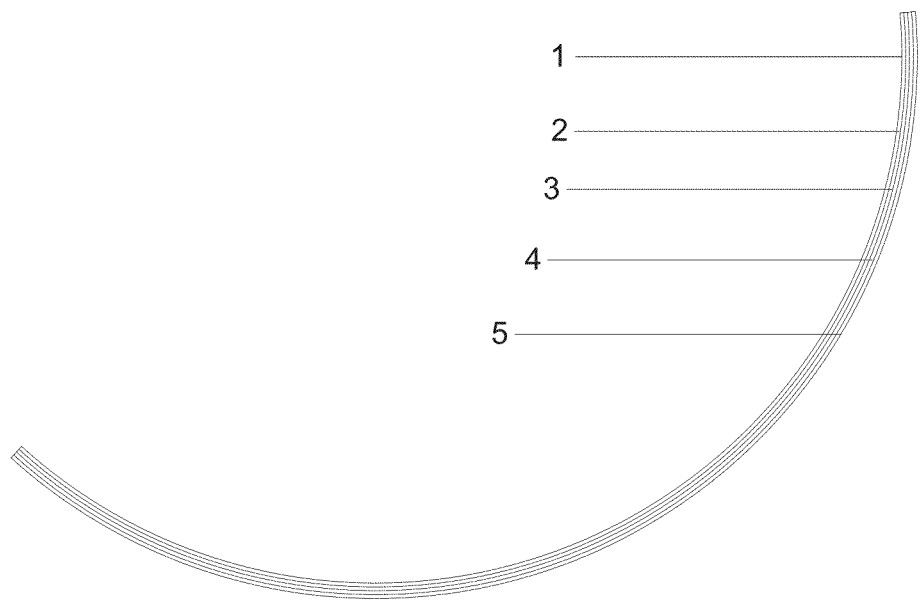
FIG. 5 shows a side view of an Absorbent Article that is Pedestal Shaped.

FIG. 5 shows a side view of an Absorbent Article that is Pedestal Shaped, which is an oval shape in which the exterior silhouette or three-dimensional outline of an item has a top end and a bottom end with the top end being curved outward and widest, continuing and becoming more narrow, and then continuing and becoming wider at the bottom end. FIG. 5 discloses a top sheet 1, which faces the body of the user, an ADL 2, and SAP/Fluff 3. The top sheet 1, ADL 2, and SAP/Fluff 3 are located on top of Air-Laid Paper 4, and a bottom sheet 5, which touches the garment and includes the Back Sheet Cloaking Device (not shown).

Figure 6:
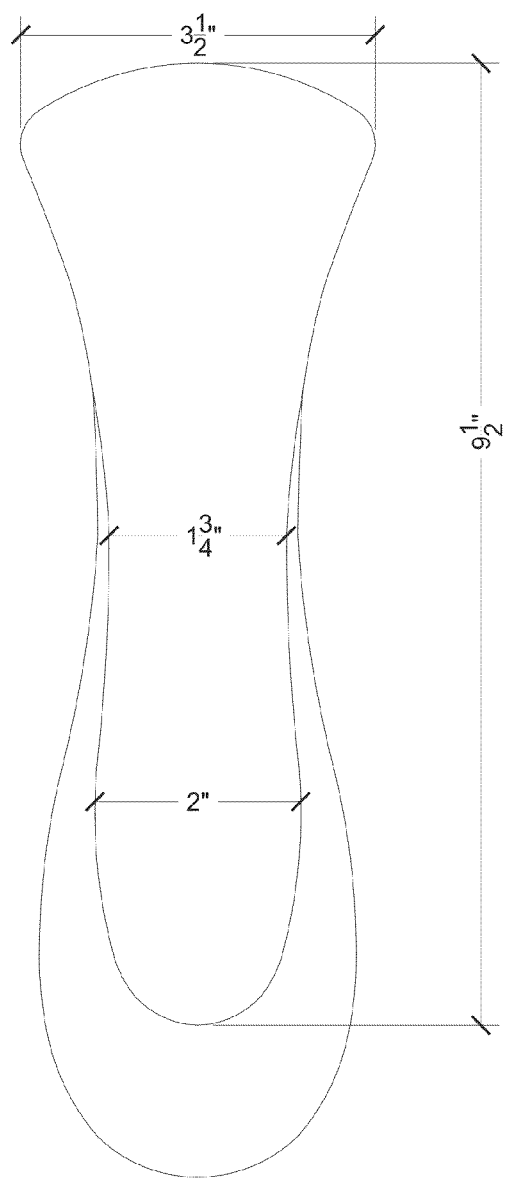
FIG. 6 shows a frontal view of an Absorbent Article that is Tapered Pedestal Shaped with measurements for one embodiment.

FIG. 6 shows a frontal view of an Absorbent Article that is Tapered Pedestal Shaped, which is an oval shape in which the exterior silhouette or three-dimensional outline of an item has a top end and a bottom end with the top end being curved outward and widest, continuing and becoming more narrow, and continuing and becoming slightly wider at the bottom end, with measurements for one embodiment. The top end of the Tapered Pedestal Shape is significantly wider than the bottom end. To note, the measurements included in this embodiment include 3.5" at the top end, which incorporates the Pubic and Vaginal Hair Hiding Device 7 (not shown).

Figure 7:
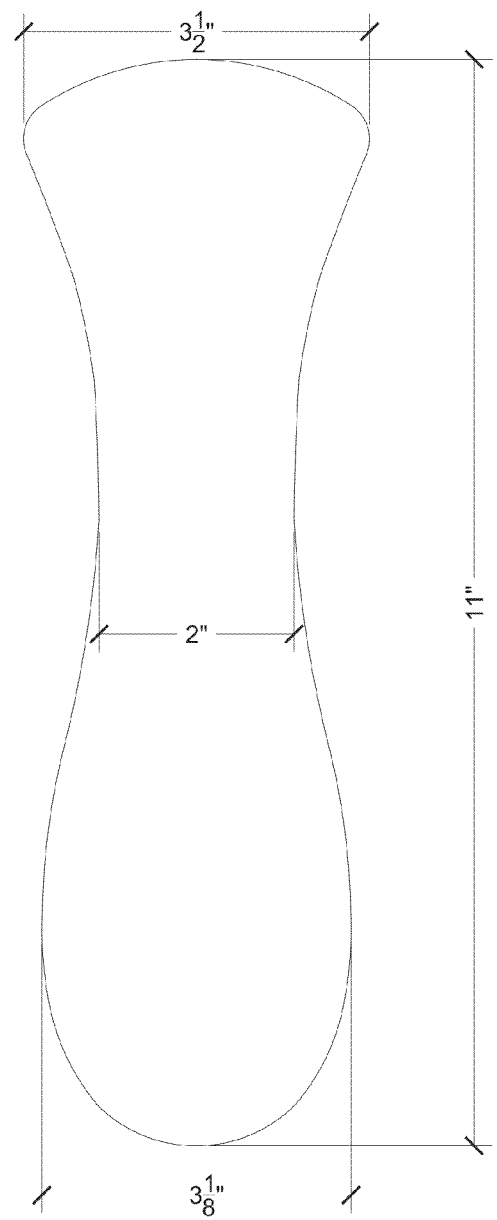
FIG. 7 shows a frontal view of an Absorbent Article that is Pedestal Shaped with measurements for one embodiment.

FIG. 7 shows a frontal view of an Absorbent Article that is Pedestal Shaped, which is an oval shape in which the exterior silhouette or three-dimensional outline of an item has a top end and a bottom end with the top end being curved outward and widest, continuing and becoming more narrow, and then continuing and becoming wider at the bottom end, with measurements for one embodiment. To note, the measurements included in this embodiment include 3.5" at the top end, which incorporates the Pubic and Vaginal Hair Hiding Device (not shown).

Figure 8:
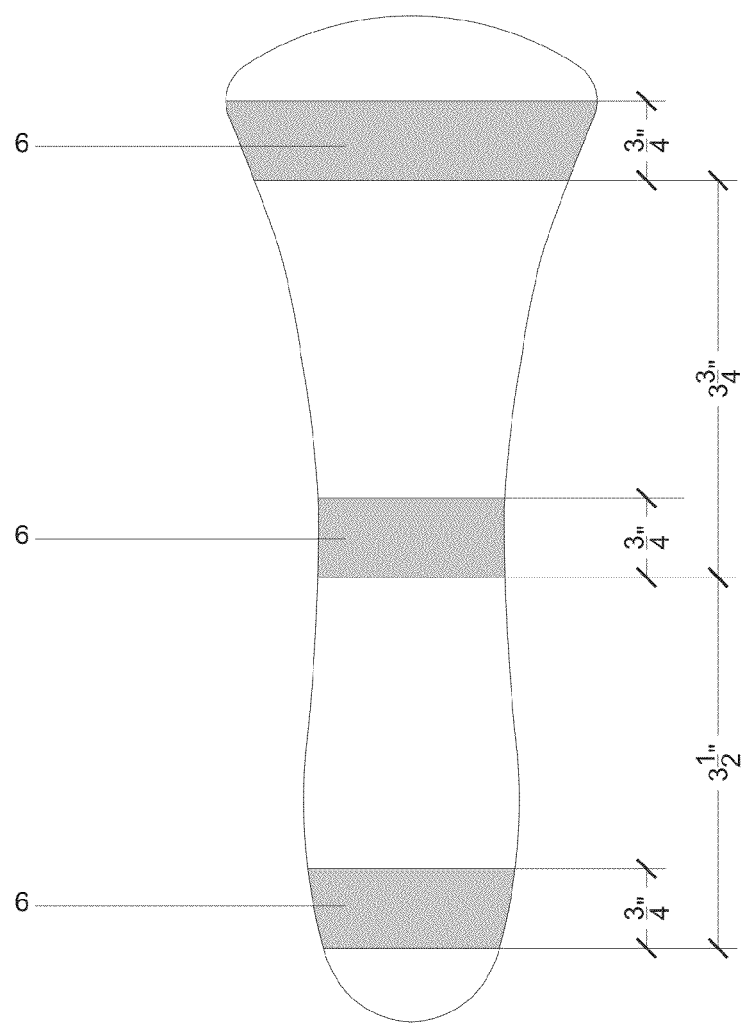
FIG. 8 shows a frontal view of an Absorbent Article that is Tapered Pedestal Shaped, the location and placement of adhesive strips, and the measurements of one embodiment.

FIG. 8 shows a frontal view of an Absorbent Article that is Tapered Pedestal Shaped, which is an oval shape in which the exterior silhouette or three-dimensional outline of an item has a top end and a bottom end with the top end being curved outward and widest, continuing and becoming more narrow, and continuing and becoming slightly wider at the bottom end, the location and placement of adhesive strips 6, and the measurements of one embodiment.

Figure 9:
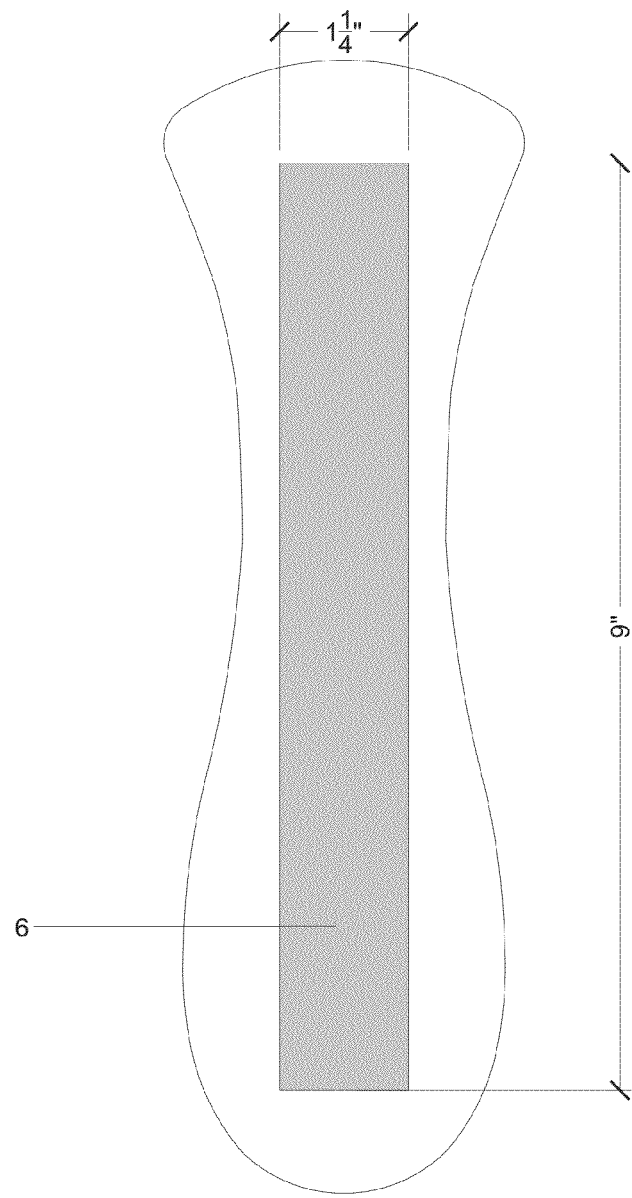
FIG. 9 shows a frontal view of an Absorbent Article that is Pedestal Shaped the location and placement of adhesive strips 6, and the measurements of one embodiment.

FIG. 9 shows a frontal view of an Absorbent Article that is Pedestal Shaped, which is an oval shape in which the exterior silhouette or three-dimensional outline of an item has a top end and a bottom end with the top end being curved outward and wide, continuing and becoming more narrow, and then continuing and becoming wider at the bottom end, the location and placement of adhesive strips 6, and the measurements of one embodiment.

Figure 10:
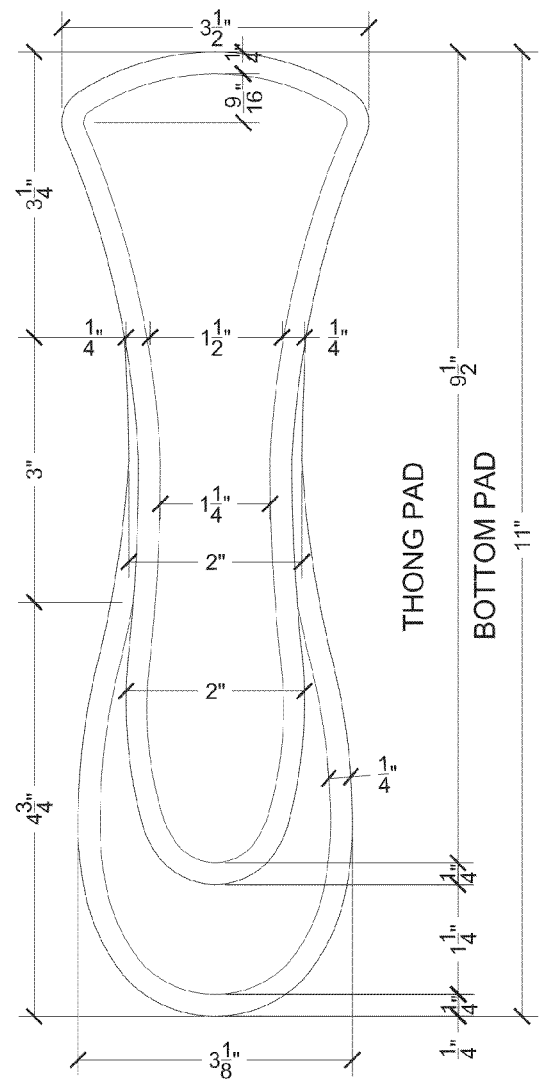
FIG. 10 shows a frontal view of an Adaptable Absorbent Article with two Absorbent Articles and the measurements of one embodiment.

FIG. 10 shows a frontal view of the Adaptable Absorbent Article with two Absorbent Articles that can be attached together and/or separated by the user so any one of the Absorbent Articles can be used separately and alone, which provides the user with maximum flexibility of use to conform to the user's body and garment type, and the measurements of one embodiment. One of the Absorbent Articles of the Adaptable Absorbent Article is Tapered Pedestal Shaped, which is an oval shape in which the exterior silhouette or three-dimensional outline of an item has a top end and a bottom end with the top end being curved outward and widest, continuing and becoming more narrow, and continuing and becoming slightly wider at the bottom end. The top end of the Tapered Pedestal Shaped is significantly wider than the bottom end. The other Absorbent Article of the Adaptable Absorbent Article in FIG. 10 is Pedestal Shaped, which is an oval shape in which the exterior silhouette or three-dimensional outline of an item has a top end and a bottom end with the top end being curved outward and wide, continuing and becoming more narrow, and then continuing and becoming wider at the bottom end.

Figure 11:
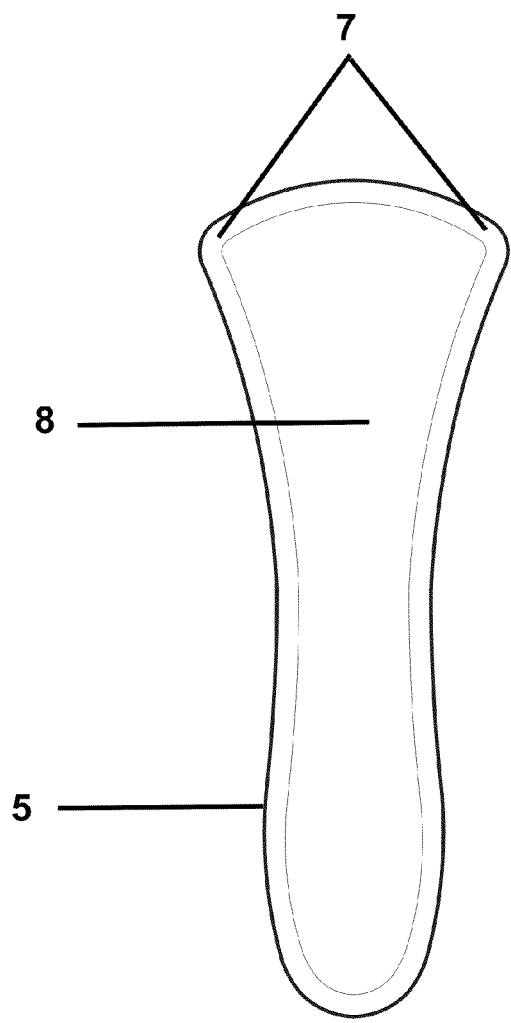
FIG. 11 shows a frontal view of the bottom sheet of an Absorbent Article that is Tapered Pedestal Shaped with a Pubic and Vaginal Hair Hiding Device and Back Sheet Cloaking Device.

FIG. 11 shows a frontal view of the bottom sheet 5 of an Absorbent Article that is Tapered Pedestal Shaped with a Pubic and Vaginal Hair Hiding Device 7 and Back Sheet Cloaking Device 8.

Figure 12:
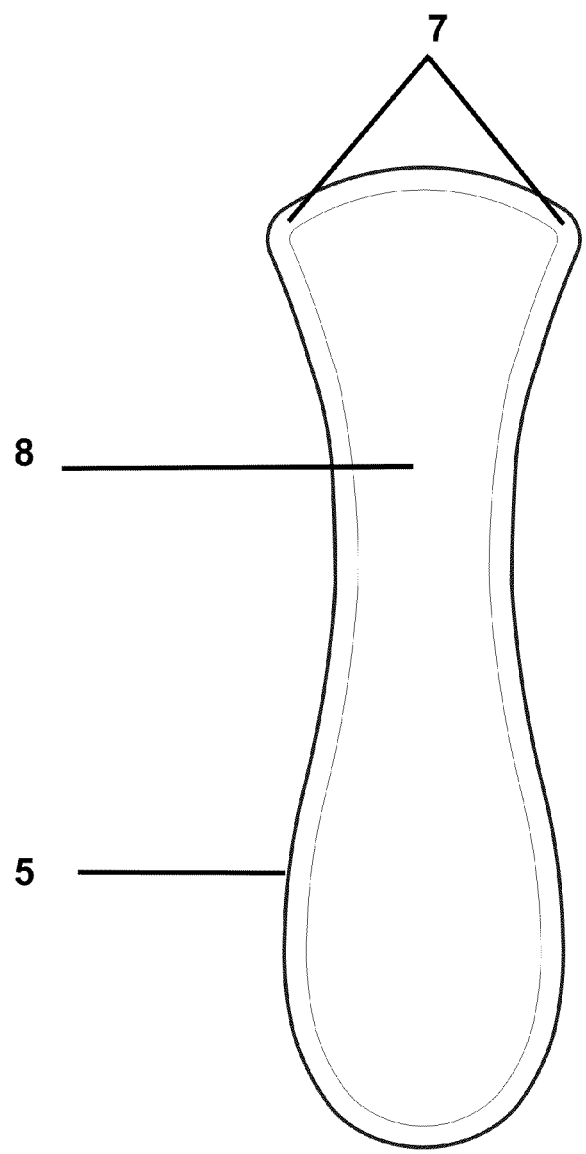
FIG. 12 shows a frontal view of the bottom sheet of an Absorbent Article that is Pedestal Shaped with a Pubic and Vaginal Hair Hiding Device and Back Sheet Cloaking Device.

FIG. 12 shows a frontal view of the bottom sheet 5 of an Absorbent Article that is Pedestal Shaped with a Pubic and Vaginal Hair Hiding Device 7 and Back Sheet Cloaking Device 8.

COMPONENT LIST

| Component No. or Letter | Component Description |
| --- | --- |
| A | Absorbent Article that is Pedestal Shaped |
| B | Absorbent Article that Tapered Pedestal Shaped |
| 1 | Top Sheet |
| 2 | ADL |
| 3 | SAP/Fluff |
| 4 | Air-Laid Paper |
| 5 | Bottom Sheet |
| 6 | Adhesive Strip |
| 7 | Pubic and Vaginal Hair Hiding Device |
| 8 | Back Sheet Cloaking Device |

DEFINITIONS

An "Absorbent Article" is defined as incontinence pads, absorbent personal pads for involuntary bladder elimination, feminine guards for incontinence, catamenial products, sanitary napkins, maxi pads, mini pads, liners, pantiliners, pads, nursing pads, menstruation tampons, sanitary tampons, tampons, feminine hygiene pads, menstruation pads, sanitary pads, menstrual underwear, adult diapers, disposable adult diapers, disposable diapers for incontinence, incontinence diapers, personal hygiene products, feminine hygiene products, male hygiene products, incontinence garments, incontinence products, and multi-purpose pads.

"Absorbent Personal Pads For Involuntary Bladder Elimination" are defined as Pads that can absorb urine, bodily discharges, or other liquids.

An "Adaptable Absorbent Article" is defined as at least two Absorbent Articles that can be attached together and/or separated by the user so any one of the Absorbent Articles can be used separately and alone, which provides the user with maximum flexibility of use to conform to the user's body and garment type.

"Adhesive Strips" are defined as one or more strips of adhesive material, such as glue, that can be produced in a variety of shapes, such as a circle, square, triangle, rectangle, quadrilateral, or other.

"ADL" is defined as an acquisition distribution layer, which spreads out the urine onto the SAP.

"Air-Laid Paper" is defined as a textile-like material that is categorized as a nonwoven fabric made from fluff pulp.

A "Back Sheet Cloaking Device" is defined as the back sheet of an Absorbent Article that is at least one of skin color, nude color, skin tone, flesh tone, tan, or brown colored.

"Catamenial Products" are defined as products related to menstruation and/or female hygiene.

"Feminine Guards For Incontinence" are defined as thin or ultra thin Pads.

"Fluff" is defined as a material that is absorbent such as cotton.

"Incontinent Pads" are defined as synthetic or non-synthetic materials, such as cotton, plastic, and/or other materials that, when put together, can absorb urine, bodily discharges, or other liquids.

"Liners" are defined as Pads that are made for daily use and/or use on the last day of a woman's period.

"Maxi Pads" are defined as Pads that can absorb a large amount of liquid from menstruation, and are usually thick but as SAP gets more sophisticated can be thinner.

"Mini Pads" are defined as Pads that absorb a small amount of liquid from menstruation, and are thin and comfortable.

A "Non-Symmetrical Silhouette" is defined as one that is not the same on both sides (i.e. left and right) or top and bottom.

"Nursing Pads" are defined as Pads that placed within a woman's bra in order to absorb and capture milk leaking from the woman's breast(s).

"Pads" are defined as synthetic or non-synthetic materials, such as cotton, plastic, and/or other materials that, when put together, can absorb urine, bodily discharges, or other liquids.

"Pantiliners" are defined as Pads that are made for daily use and/or use on the last day of a woman's period "Pedestal Shaped" is defined as an exterior silhouette, or three or two-dimensional outline of an item that has a top end and a bottom end with the top end being curved outward at the top and the top section is the widest section from left to right, when continuing down the pedestal shape and becoming more narrow, and then continuing downward and becoming wider and rounded at the bottom end.

A "Pubic and Vaginal Hair Hiding Device" is defined as additional material continued left and right of the top side of the Absorbent Article that is used to conceal hair located around the pubic and vaginal regions of the user, which is usually not covered, but is, in fact, disclosed and publicly displayed when utilizing the prior art referenced above.

"Sanitary Napkins" are defined as Pads that can absorb menstruation flow and/or discharge.

"SAP" is defined as a super absorbent polymer, which is a sand like substance that "fluffs up" in size when such substance encounters liquid, that makes the Absorbent Article absorbent.

"Tapered Pedestal Shaped" is defined as an exterior silhouette, or three or two-dimensional, outline of an item that has a top end and a bottom end with the top end being curved upward and outward and top section is the widest from left to right, continuing downward and becoming more narrow, and continuing downward and becoming slightly wider at the bottom end. The top end of a Tapered Pedestal Shape is significantly wider than the bottom end.

What is claimed is:

1. An adaptable absorbent article for wearing in a crotch region of a user, consisting of:
   a top pad and a bottom pad selectively attached in a stack wherein each of the top pad and bottom pad consists of:
      a liquid pervious top sheet that faces the user;
      a middle layer consisting of an acquisition distribution layer ("ADL"), a super absorbent polymer ("SAP") and/or fluff, and an air-laid paper;
      a completely or substantially liquid impervious back sheet cloaking device;
      wherein the middle layer is positioned between said liquid pervious top sheet and said liquid impervious back sheet cloaking device; and
      wherein said liquid impervious back sheet cloaking device is connected via sewing to said liquid pervious top sheet on the side of the absorbent article that faces the undergarment; and
      adhesive on the back sheet cloaking device such that the top pad and bottom pad can be attached separately onto an undergarment;
   wherein the top pad includes a pubic and vaginal hair hiding device allowing for the top pad to cover hair in the pubic, pubic bone, and vaginal area;
   wherein the top pad has a tapered pedestal shape such that that the top section of said top pad is significantly wider than the bottom section of said to pad such that it is shaped to fit within a thong undergarment;

wherein the bottom pad has a pedestal shape such that the top and bottom sections of said bottom pad are selectively sized to be wider than the middle section of the bottom pad; and wherein the widths of the top sections of the top and bottom pads are the same, and the width of the bottom section of the bottom pad is wider than the width of the bottom section of the top pad such that the bottom pad covers a larger area of the crotch region than the top pad.

2. The adaptable absorbent article of claim 1 wherein the width of the top section of each of the top and bottom pads is one of the following:

at least 2";
at least 3";
at least 4";
at least 5";
between 2" and 3";
between 3" and 4"; or
between 4" and 5".

3. The adaptable absorbent article of claim 1 wherein said back sheet cloaking device has a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red falls within the range bounded at the lower end of 140 and the upper end of 255, said Green falls within the range bounded at the lower end of 100 and the upper end of 255, and said Blue falls within the range bounded at the lower end of 80 and the upper end of 255.

4. The adaptable absorbent article of claim 1 wherein said back sheet cloaking device of each of the top and bottoms pads has a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red falls within the range bounded at the lower end of 150 and the upper end of 245, said Green falls within the range bounded at the lower end of 110 and the upper end of 245, and said Blue falls within the range bounded at the lower end of 90 and the upper end of 245.

5. The adaptable absorbent article of claim 1 wherein said back sheet cloaking device of each of the top and bottoms pads has a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red falls within the range bounded at the lower end of 210 and the upper end of 255, said Green falls within the range bounded at the lower end of 140 and the upper end of 255, and said Blue falls within the range bounded at the lower end of 140 and the upper end of 255.

6. The adaptable absorbent article of claim 1 wherein said back sheet cloaking device of each of the top and bottoms pads has a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red falls within the range bounded at the lower end of 220 and the upper end of 255, said Green falls within the range bounded at the lower end of 150 and the upper end of 245, and said Blue falls within the range bounded at the lower end of 150 and the upper end of 245.

7. The adaptable absorbent article of claim 1 wherein said back sheet cloaking device of each of the top and bottoms pads has a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red falls within the range bounded at the lower end of 110 and the upper end of 255, said Green falls within the range bounded at the lower end of 60 and the upper end of 255, and said Blue falls within the range bounded at the lower end of 50 and the upper end of 255.

8. The adaptable absorbent article of claim 1 wherein said back sheet cloaking device of each of the top and bottoms pads has a color composition defined in coordinates Red (which is quantified in the range from a minimum of 0 to a maximum of 255), Green (which is quantified in the range from a minimum of 0 to a maximum of 255), and Blue (which is quantified in the range from a minimum of 0 to a maximum of 255), and further that said Red falls within the range bounded at the lower end of 120 and the upper end of 255, said Green falls within the range bounded at the lower end of 70 and the upper end of 245, and said Blue falls within the range bounded at the lower end of 60 and the upper end of 245.

9. The adaptable absorbent article of claim 1 wherein at least one element of the adaptable absorbent article is liquid absorbent.

10. The adaptable absorbent article of claim 1 wherein at least one element of the adaptable absorbent article is odor absorbent, scented or a freshness device.

11. The adaptable absorbent article of claim 1 wherein at least one element of the adaptable absorbent article provides protection against UV rays.

* * * * *